United States Patent
Castro et al.

(10) Patent No.: US 10,004,568 B2
(45) Date of Patent: Jun. 26, 2018

(54) ARTICULATING ROBOTIC PROBES

(71) Applicant: MEDROBOTICS CORPORATION, Raynham, MA (US)

(72) Inventors: Michael Salvatore Castro, Plymouth, MA (US); Joseph Karcsmar, Raynham, MA (US); R. Maxwell Flaherty, Auburndale, FL (US); J. Christopher Flaherty, Auburndale, FL (US)

(73) Assignee: MEDROBOTICS CORPORATION, Raynham, MA (US)

( * ) Notice: Subject to any disclaimer, the term of this patent is extended or adjusted under 35 U.S.C. 154(b) by 0 days. days.

(21) Appl. No.: 14/892,750

(22) PCT Filed: Dec. 19, 2014

(86) PCT No.: PCT/US2014/071400
§ 371 (c)(1),
(2) Date: Nov. 20, 2015

(87) PCT Pub. No.: WO2015/102939
PCT Pub. Date: Jul. 9, 2015

(65) Prior Publication Data
US 2016/0256226 A1    Sep. 8, 2016

Related U.S. Application Data

(60) Provisional application No. 61/921,858, filed on Dec. 30, 2013, provisional application No. 62/008,453, filed on Jun. 5, 2014.

(51) Int. Cl.
*A61B 90/50* (2016.01)
*A61B 17/34* (2006.01)
(Continued)

(52) U.S. Cl.
CPC .......... *A61B 90/50* (2016.02); *A61B 1/00039* (2013.01); *A61B 17/3421* (2013.01);
(Continued)

(58) Field of Classification Search
CPC .... A61B 2034/306; A61B 2017/00323; A61B 2017/00318; A61B 2017/00314;
(Continued)

(56) References Cited

U.S. PATENT DOCUMENTS 3,060,972 A   10/1962   Sheldon
3,557,780 A   1/1971    Sato
(Continued)

FOREIGN PATENT DOCUMENTS

CA   2858831    6/2013
EP   0653922    11/2005
(Continued)

OTHER PUBLICATIONS

Expo-70 Robot—Vadim Matskevich's students, http://cyberneticzoo.com/wp-content/uploads/2010/03/Expo-70-MK-1969-02-p31-3.pdf, 1969.
(Continued)

*Primary Examiner* — Thomas McEvoy
(74) *Attorney, Agent, or Firm* — Onello & Mello LLP

(57) ABSTRACT

An articulated probe assembly comprises a base, an outer support rod extending through the base, an articulating control portion at a proximal end of the outer support rod, and a steerable portion comprising a plurality of outer links coupled to a distal end of the outer support rod. The steerable portion is manipulated in response to the articulating control portion.

31 Claims, 6 Drawing Sheets

(51) Int. Cl.
*A61B 1/00* (2006.01)
*A61B 34/00* (2016.01)
*A61B 34/30* (2016.01)
*A61B 17/00* (2006.01)
*A61B 90/57* (2016.01)

(52) U.S. Cl.
CPC ............. *A61B 34/25* (2016.02); *A61B 34/30* (2016.02); *A61B 2017/003* (2013.01); *A61B 2017/00323* (2013.01); *A61B 2017/3409* (2013.01); *A61B 2017/3447* (2013.01); *A61B 2034/305* (2016.02); *A61B 2090/571* (2016.02)

(58) Field of Classification Search
CPC .... A61B 2017/00305; A61B 2017/003; A61B 1/00078; A61B 90/50
See application file for complete search history.

(56) References Cited

U.S. PATENT DOCUMENTS

| | | |
|---|---|---|
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hill |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A | 4/1987 | Iwashita |
| 4,661,032 A | 4/1987 | Arai |
| 4,666,366 A | 5/1987 | Davis |
| 4,700,693 A | 10/1987 | Lia et al. |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,193,963 A | 3/1993 | McAffee et al. |
| 5,195,968 A | 4/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,386,741 A | 2/1995 | Rennex |
| 5,448,989 A | 10/1995 | Heckele |
| 5,524,180 A | 6/1996 | Wang et al. |
| 5,759,151 A | 6/1998 | Sturges |
| 5,815,640 A | 9/1998 | Wang et al. |
| 5,841,950 A | 11/1998 | Wang et al. |
| 5,907,664 A | 5/1999 | Wang et al. |
| 5,916,147 A | 6/1999 | Boury |
| 5,957,941 A | 9/1999 | Ream |
| 6,080,181 A | 6/2000 | Jensen et al. |
| 6,132,368 A | 10/2000 | Cooper |
| 6,346,072 B1 | 2/2002 | Cooper |
| 6,837,846 B2 | 1/2005 | Jaffe et al. |
| 6,837,847 B2 | 1/2005 | Ewers et al. |
| 7,357,774 B2 | 4/2008 | Cooper |
| 7,789,875 B2 | 9/2010 | Brock et al. |
| 7,819,885 B2 | 10/2010 | Cooper |
| 7,850,642 B2 | 12/2010 | Moll et al. |
| 7,854,109 B2 | 12/2010 | Zubiate et al. |
| 7,854,738 B2 | 12/2010 | Lee et al. |
| 7,867,241 B2 | 1/2011 | Brock et al. |
| 7,946,546 B2 | 5/2011 | Zubiate et al. |
| 8,100,031 B2 | 1/2012 | Zubiate et al. |
| 8,192,422 B2 | 6/2012 | Zubiate et al. |
| 8,459,138 B2 | 6/2013 | Zubiate et al. |
| 9,364,955 B2 | 6/2016 | Oyola et al. |
| 2002/0091374 A1 | 7/2002 | Cooper |
| 2005/0021050 A1 | 1/2005 | Cooper |
| 2005/0273084 A1* | 12/2005 | Hinman ................ A61B 1/008 606/1 |
| 2008/0147091 A1 | 6/2008 | Cooper |
| 2008/0188868 A1* | 8/2008 | Weitzner ............ A61B 1/0014 606/130 |
| 2008/0245173 A1 | 10/2008 | Schwerin et al. |
| 2009/0171151 A1 | 7/2009 | Choset et al. |
| 2009/0287043 A1* | 11/2009 | Naito ................ A61B 1/0052 600/104 |
| 2009/0326449 A1 | 12/2009 | Wang et al. |
| 2010/0262161 A1 | 10/2010 | Danitz et al. |

(56) References Cited

U.S. PATENT DOCUMENTS

| | | | |
|---|---|---|---|
| 2010/0274078 A1* | 10/2010 | Kim | A61B 1/00149 600/102 |
| 2011/0028990 A1 | 2/2011 | Cooper | |
| 2011/0066161 A1 | 3/2011 | Cooper | |
| 2011/0152613 A1 | 6/2011 | Zubiate et al. | |
| 2011/0184241 A1 | 7/2011 | Zubiate et al. | |
| 2011/0313243 A1 | 12/2011 | Zubiate et al. | |
| 2014/0012287 A1 | 1/2014 | Oyola et al. | |
| 2014/0318299 A1 | 10/2014 | Oyola et al. | |
| 2015/0150633 A1 | 6/2015 | Castro et al. | |
| 2017/0015007 A1 | 1/2017 | Anderson et al. | |

FOREIGN PATENT DOCUMENTS

| | | |
|---|---|---|
| EP | 1015068 | 9/2011 |
| WO | 2012015659 | 2/2012 |
| WO | 2013184560 | 12/2013 |

OTHER PUBLICATIONS

Conductor Robot, http://cyberneticzoo.com/wp-content/uploads/2010/03/Ticket-robot-russian-1973.pdf, 1973.

Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.

Lee E. Weiss, Arthur C. Sanderson, Charles P. Neuman, "Dynamic Sensor Based Control of Robots with Visual Feedback", IEEE Journal of Robotics and Automation, 1987, p. 404-417.

Jean-Jacques E. Slotine, Weiping Li, "Composite adaptive control of robot manipulators", Automatica; Nonlinear Systems Laboratory, Massachusetts Institute of Technology, Cambridge, MA 02139, U.S.A., 1989, p. 509-519.

Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.

Xu Hongbin, "Stability and performance robustness analysis of hybrid control for robot manipulators", Journal of UEST of China, vol. 22 No. 5, Oct. 1993, p. 501-505.

Francois Chaumette, Patrick Rives, Bernard Espiau, "Positioning of a Robot With Respect to an Object, Tracking It and Estimating Its Velocity by Visual Servoing", IEEE International Conf. on Robotics and Automation, 1991, p. 2248-2253.

A.V. Timofejev, N.V. Ivanova, "Expert System of the Control Programs Designing of Adaptive Robots", The Lenigrand Institute of Aircraft Instrumentation, 1991, p. 912-915.

W Szczepiński, "Theory of polyhedrons of positioning accuracy of manipulators", Mechanism and Machine Theory; Institute of Fundamental Technological Research, Polish Academy of Sciences, 00-049 Warsaw, Swietokrzyska 21, Poland, 1991, p. 697-709.

Junji Furusho, Hiroshi Nagao, Naruse Makoto, "Multivariable Root Loci of Control Systems of Robot Manipulators with Flexible Driving Systems*: Distortion Feedback", JSME International Journal, 1992, p. 65-73.

Potemkin, E., Astafurov, P., Osipov, A., Malenkov, M., Mishkinyuk, V., Sologub, P., "Remote-controlled robots for repair and recovery in the zones of high radiation levels", Robotics and Automation, IEEE, 1992, p. 80-82.

S. L. Shishkin, "Adaptive control of a biped robot walking across a horizontal plane", International Journal of Adaptive Control and Signal Processing, 1992, p. 259-264.

Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.

Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.

J.D. Moon, D.W. Cho, "A component mode synthesis applied to mechanisms for an investigation of vibration", Journal of Sound and Vibration; Department of Mechanical Engineering, Pohang Institute of Science and Technology, Pohang, Korea, 1992, p. 67-79.

Timopheev, A.V., Prokhorov, D.V., "Neural networks processing systems in recognition and control problems", Neuroinformatics and Neurocomputers; IEEE, 1992, p. 820-828.

Jianguo Fu, Naresh K. Sinha, "An iterative learning scheme for motion control of robots using neural networks: A case study", Journal of Intelligent & Robotic Systems, 1993, p. 375-398.

Troccaz, J. Lavallee, S. Hellion, E., "A passive arm with dynamic constraints: a solution to safety problems in medical robotics", Systems Engineering in the Service of Humans', Conference Proceedings, 1993, p. 166-171.

Swarup, M. Gopal, "Comparative study on linearized robot models", Journal of Intelligent & Robotic Systems, 1993, p. 287-300.

H. Azaria, A. Dvir, "Algorithm optimization using a rule-based system. A case study: The Direct Kinematic Solution in robotics", Journal of Intelligent & Robotic Systems, 1993, p. 309-324.

Erick Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.

K. Periyasamy, V. S. Alagar, T. D. Bui, "A formal framework for design and verification of robotic agents", Journal of Intelligent & Robotic Systems, 1993, p. 173-200.

S. Nicosia, A. Tornambè, P. Valigi, "State estimation in robotic manipulators: Some experimental results", Journal of Intelligent & Robotic Systems,, 1993, p. 321-351.

Dimitrios M. Emiris, Vassilios D. Tourassis, "Singularity-robust decoupled control of dual-elbow manipulators", Journal of Intelligent & Robotic Systems, 1993, p. 225-243.

M.M. Bayoumi, "Adaptive Control of Robots with Rigid Links: A Status Report", Department of Electrical Engineering, Queen's University, Ontario, Canada (IEEE), 1993, p. 232-236.

Y. Edan, B. A. Engel, G. E. Miles, "Intelligent control system simulation of an agricultural robot", Journal of Intelligent & Robotic Systems, 1993, p. 267-284.

Chun-Yi Su, "Adaptive sliding mode control of nonlinear robotic systems with time-varying parameters", Systems and Control Letters; Department of Mechanical Engineering, University of Victoria, Victoria, B.C. Canada V8W 3P6, 1993, p. 35-41.

Yalou Huang; Guizhang Lu, "Force Analysis and Hybrid Control Scheme for Multiple Robot Manipulators", Artificial Intelligence and Robotics Research Laboratories; Dept of Computer and System Sciences; Nankai University, China (Proceedings of the 1993 IEEE/RSJ International Conference on Intelligent Robots and Systems in Japan), 1993, p. 1530-1534.

C.M. Lim; T. Hiyama, "Experimental implementation of a fuzzy logic control scheme for a servomotor", Mechatronics; Department of Electronic Engineering, Ngee Ann Polytechnic, Singapore 2159 Singapore.

E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6 2AY, U.K., 1993, p. 329-342.

A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.

L. Behera, M. Gopal, Santanu Chaudhury, "Trajectory tracking of robot manipulator using Gaussian networks", Dept. of Electrical Engineering, Indian Institute of Technology, Delhi, Hauz Khas, New Delhi 110 016, India, 1993.

E. V. Panteley, A. A. Stotsky, "Adaptive trajectory/force control scheme for constrained robot manipulators", International Journal of Adaptive Control and Signal Processing, 1993, p. 489-496.

Filaretov, V.F., "A Synthesis of Adaptive Control Systems for Industrial Robots", Electronic Mfg Technology Symposium, 1993, p. 168-171.

(56) References Cited

OTHER PUBLICATIONS

S. Zenkevich, A. Maximov, A. Nazarova, A. Korshunov, "Control of robot-based assembly cell", Lecture Notes in Control and Information Sciences, 1993, p. 418-427.
D.E. Whitney, "The Mathematics of Coordinated Control of Prosthetic Arms and Manipulators", Asme Publication, 1972.
Shapiro, "Digital Technology Enables Robots to See", Computer Design, 1978.
Bejczy, A. K., Salisbury, Jr., J. K., "Kinesthetic Coupling Between Operator and Remote Manipulator", Advances in Computer Technology, 1980.
"An Improved CT-Aided Stereotactic Neurosurgery Technique", Fifth Annual Symposium on Computer Applications in Medical Care, 1981, p. 591-595.
Michael L. Thodes, Ph.D, "Stereotactic Neurosurgery Using 3D Image Data From Computed Tomography", Journal of Medical Systems, 1982, p. 106-118.
Salisburg, Jr., J. Kenneth, "Kinematic and Force Analysis of Articulated Hands", 1982.
"Minicomputer Control Robot's Six Electrohydraulic Servoactuators", Hydraulics & Pneumatics, 1982, p. 53-58.
F.M. Kulakov, "Modeling Robot Control in Assembly Operations", Modern Robot Engineering, Moscow, MIR Publishers, 1982, p. 100-116.
Bejczy et al., "Controlling Remote Manipulators Through Kinesthetic Coupling", Computers in Mechanical Engineering, 1983, p. 48-60.
L.E. Weiss, "Dynamic Visual Servo Control of Robots: an adaptive image-based approach, Technical Report", Part 1 Carnegie Mellon, 1984.
Dennis E. Bullard, "CT-Guided Stereotactic Biopsies Using a Modified Grame and Gildenberg Techniques", Journal of Neurology, Neurosurgery and Psychiatry, 1984, p. 590-595.
M. Caporali et al., "Design and Construction of a Five Fingered Robotic Hand", Robotics Age, 1984, p. 14-20.
Salisbury, Jr., J. K., "Design and Control of an Articulated Hand", International Symposium on Dessign and Synthesis, 1984.
L. Dade Lunsford, M.D., "Stereotactic Exploration of the Brain in the Era of Computed Tomography", Surg. Neurol, 1984, p. 222-230.
Jacobsen, S.C., Iversen, E.K., Knutti, D. F., Johnson, R.T., Biggers, K. B., "Design of the Utah/MIT Dexterous Hand", Conf. on Robotics and Automation, 1986.
S. Hayati, M. Mirmirani, "Improving the Absolute positioning Accuracy of Robot Manipulators", Journal of Robotic Systems, 1986, p. 397-413.
Vertut, J., Coiffet, P., "Teleoperations and Robotics Evolution and Development", Robot Technology, 1986, p. 191-194.
L.E. Weiss; A.C. Sanderson, "Dynamic Sensor-based Control of Robots with Visual Feedback", IEEE Journal of Robotics and Automation, 1987, p. 5.
Townsend, W.T., Salisbury, Jr. J. K., "The Effect of Coulomb Friction and Stiction on Force Control", Conf. on Robotics and Automation, 1987.
P. Rives, F. Chaumette, B. Espiau, "Visual Servoing Based on a Task Function Approach", International Symposium on Experimental Robotics (Canada), 1989.
B.L. Davies, R.D. Hibberd, A. Timoney, J.E.A. Wickham, "A surgeon robot for prostatectomies", Proc. of 2nd Int. Conference on Robotics in Medicine (UK), 1989.
J.T. Feddema, C.S.G. Lee, O.R. Mitchell, "Automatic selection of image features for visual servoing of a robot manipulator", Conf. IEEE Robotics and Automation (USA), 1989, p. 14-19.
J.T. Feddema, O.R. Mitchell, "Vision-Guided Servoing with Feature-Based Trajectory Generation", IEEE Transaction on Robotics and Automation, 1989.
Pierre J. de Smet, Eugene I. Rivin, Yongle Lou, D. Kegg, "Robot Performance as Influenced by Mechanical System", CIRP Annals—Manufacturing Technology, 1990, p. 383-386.
Mills, J.K., "Hybrid actuation of robotic manipulators: an integral manifold control approach", Intelligent Control, IEEE, 1990, p. 817-823.
John T. Feddema, C. S. George Lee, "Adaptive Image Feature Prediction and Control for Visual Tracking with a Hand-eye Coordinated Camera", IEEE Transactions on Systems, man, and Cybernetics, 1990, p. 1172-1183.
Rafiqul I. Noorani, "Microcomputer-based robot arm control", Mathematical and Computer Modelling, 1990, p. 450-455.
Elysseev S., Kuznetzov, N., Lukyanov A., "Control of Robot Vibrations", 1990.
C. Samson, B. Espiau, "Robot Control: The Task Function Approach", Oxford Univ., 1990.
Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.
B. Espiau, F. Chaumette, P. Rives, "A new approach to visual servoing in robotics", Research Report; IRISA/INRIA (France), 1990.
Korikov, Anatoliim, Syriamkin, Vladimiri, Titov, Vitaliis, "Correlation robot vision systems", 1990, p. 264.
Sadegh N, Hopowitz R, "Stability and robustness analysis of a class of adaptive controller for robotic manipulator", The International Journal of Robotics Research, 1990.
Rocheleau, D.N., Crane, C.D., III, "Development of a graphical interface for robotic operation in a hazardous environment", Systems, Man, and Cybernetics, 1991, p. 1077-1081.
J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., Kobayashi, H., "An inspection robot for feeder cables-snake like motion control", Industrial Electronics, Control, Instrumentation, and Automation, 1992, p. 849-852.
P. Kazanzides, J. Zuhars, B. Mittelsstadt, R.H. Taylor, "Force sensing and control for a surgical robot", IEEE conference on Robotics and Automation (Nice), 1992, p. 612-617.
Vsevolod I. Astafyev Farus, Yakutsk, Russia Yuri M. Gorsky, "Homeostatics", Cybernetics and applied systems, 1992, p. 7-22.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME international journal, 1992, p. 406-412.
Ph, Cinquin, et. al, IGOR: Image Guided Operating Robot. Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.
Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
Alberto Rovetta, Xia Wen, Telemanipulation Control of a Robotic Hand With Cooperating Fingers by Means of Telepresence With a

(56) References Cited

OTHER PUBLICATIONS

Hybrid Virtual-Real Structure, RoManSy 9: Proceedings of the Ninth CISM-IFToMM Symposium on Theory and Practice of Robots and.
James K. Mills, Hybrid Actuator for Robot Manipulators: Design, Controland Performance, Robotics and Automation, IEEE Conference, 1993, p. 19-38.
Pietro Fanghella, Carlo Galletti, An Approach to Symbolic Kinematics of Multiloop Robot Mechanisms, RoManSy9, 1993, p. 33-40.
Yozo Fujino, Pennung Warnitchai, B.M. Pacheco, Active Stiffness Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicapped blind persons with physical guidance and activity choices", Journal of Developmental and Physical Disabilities, 1993, p. 337-348.
Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian , Generalized Dynamic Model for Multibodies Manipulator, 1993.
F.M. Kulakov, Russian Research on Robotics, Intelligent Autonomous Systems, 1995, p. 53-62.
Shevtsova N.A., Faure A., Klepatch A.A., Podladchikova L.N., Rybak I.A. , Model of Foveal Visual Preprocessor, Intelligent Robots and Computer Vision XIV: Algorithms, Techniques, Active Vision, and Materials Handling, 1995, p. 588-596.
Reynolds, O., "On Efficiency of Belts or Straps as Communicators of Work", The Engineer, 1874, p. 396.
Swift, H. W., "Power Transmission by Belts: An Investigation of Fundamentals", The Institution of Mechanical Engineers, 1928.
Smith, G. A. et al., "Surgery", 1950, p. 817-821.
"Baby Robot", http://cyberneticzoo.com/wp-content/uploads/2010/03/Ticket-robot-russian-1973.pdf, 1970.
Rajac, "Variable-Pitch Transfer Mechanism", IBM Technical Disclosure Bulletin, 1974.
ZH Luo , "Theoretical and Experimental Study on Control of Flexible Robot Arms Using Direct Strain Feedback", 1992.
Bu Yonghong, Wang Yi, "The Identification of Geometric Link Parameters of Robot Manipulators", ACTA Automatica Sinica, 1992.
Zheng Nanning Wang Long Hu chao Liu Jianqin, "Improved BP Neural Net and Its Application to Handwritten Numeral Recognition", 1992.
Stefano Chiaverini, Bruno Siciliano, Olav Egeland, Robot Control in Singular Configurations—Analysis and Experimental Results, Experimental Robotics II, 1993, p. 25-34.
Antonio Bicchi, J. Kenneth Salisbury, David L. Brock, Experimental Evaluation of Friction Characteristics With an Articulated Robotic Hand, Experimental Robotics II, 1993, p. 153-167.
Claudio Melchiorri, Gabriele Vassura, Mechanical and Control Issues for Integration of an Arm-Hand Robotic System, Experimental Robotics II, 1993, p. 136-152.
Andrew K. Rist, Ellen Y. Lin, Bartholomew O. Nnaji, Ralph Application for Surface Mount Assembly, International Journal of Flexible Manufacturing Systems, 1993, p. 27-52.
R.H. Taylor, et. al, A Model-Based Optimal Planning and Execution System With Active Sensing and Passive Manipulation for Augmentation of Human-Precision in Computer-Integrated Surgery, Lecture Notes in Control and Information Sciences; Experimental Robo.
Nobuyuki Furuya, Masatomo Matubara, An Algorithm of Motor Control by Software Servo System (2nd Report): Application to 4-Axes Scara Robot, Journal of the Japan Society of Precision Engineering , 1993, p. 423-428.
H.S. Moon, S.Y. Lee, S.J. Na, A Study on Selection of Gas Metal Arc Welding Parameters of Fillet Joints Using Neural Network, Journal of the Korean Welding Society, 1993, p. 151-160.
Byong Suk Kim, Computer-Assisted System for Accident Analysis and Mul-Function Protection in Industrial Robot, Papersearch.net (Korean Studies Information Co.), 1993, p. 61-64.
J. I. Arocena, R. W. Daniel, P. Elosegui, End Point Control of Compliant Robots, Experimental Robotics II, 1993, p. 435-449.
Ho Kyung Kim, Nonlinear Static Analysis and Determination of Initial Equilibrium States of Suspension Bridges, 1993, p. 177-186.
Gimdongha, imhyeongyo (Dong Ha Kim, Hyeon Kyo Lim) , Safe Speed Limit of Robot Arm During Teaching and Maintenance Work, 1993, p. 64-70.
Chang-Boo Kim, Seung-Hoon Lee, Inverse Dynamic Analysis of a Flexible Robot Arm With Multiple Joints by Using the Optimal Control Method, Journal of the Korean Society of Precision Engineering , 1993, p. 133-140.
Chang-Soo Han, The Optimum Design of a 6 D.O.F. Fully-Parallel Micromanipulator for Enhanced Robot Accuracy, Journal of the Korean Society of Precision Engineering , 1993, p. 42-51.
Nicholas Jackson, The Story Behind the Russian Robot Collie Patent Sketches, The Atlantic, 2011.
Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.
Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robot and CNC Machine System, Control R/D Team, Samsung Electronics, 1992, p. 1211-1214.
E.S. Jeon, S.H. Park, J.E. Oh, Singylarty Control of Robot Wrist Joints Using Euler Parameters, Journal of the Korean Society of Precision Engineering , 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong Kug Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using ARMA Prediction Model, 1992, p. 122-127.
Dae-Gab Gweon, Choong-Min Jung, Development of a Robot Wrist for the Assembly of Chamferless Parts, Journal of the Korean Society of Precision Engineering , 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.
Chang-Boo Kim, Seung-Hoon Lee, Formulation of the Equation of Motion for Flexible Robotics Arms by Using the Finite Element Method, Inha Univ., Daewoo Heavy Industries LTD, 1992, p. 233-238.
Jin-Geol Kim, A Study on the Robust Digital Tracking Control of a Robot With Flexible Joints, Journal of the Korean Society of Precision Engineering , 1992, p. 92-100.
Han-Sig Lee, The Prospects for the Future on Research of Flexible Automation and Robot System, 1992, p. 37-38.
Young Hood Joo, Seok Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.
H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.

(56) References Cited

OTHER PUBLICATIONS

Morris R. Driels, W. Swayze, S. Potter, Full-Pose Calibration of a Root Manipulator Using a Coordinate-Measuring Machine, The International Journal of Advanced Manufacturing Technology, 1993, p. 34-41.

M. Wu, B. C. Jiang, Y. R. Shiau, Controlling a Robot's Position Using Neural Networks, The International Journal of Advanced Manufacturing Technology, 1993, p. 216-226.

Joachim O. Berg, Path and Orientation Accuracy of Industrial Robots, The International Journal of Advanced Manufacturing Technology, 1993, p. 29-33.

Shaheen Ahmad, Mohamed Zribi, Lyapunov-Based Control Design for Multiple Robots Handling a Common Object, Dynamics and Control, 1993, p. 127-157.

S.D. Park, K.W. Jeong, W.K. Chung, Y. Youm, Development of a Control Method Using Both Electric and Pneumatic Actuators for a Heavy Load Handing Robot, Journal of the Korean Society of Precision Engineering , 1993, p. 14-21.

Nicolay V. Kim, Algorithms of Observation Information Synthesis, International Conference on Electronics, Informations and Communications, 1993, p. 120-124.

Sung Do Chi, Seok Pil Lee, Wang Jae Lee, San Hui Park, Hierarchical Design of Intelligent Robot System, Hankuk Aviation Univ., Yonsel Univ., 1993, p. 213-216.

Cai Zi-Xing, Jiang Zhiming, High-Level Expert System-Based Robot Planning, 1993.

Yong-Deuk Seo, Dong-Joon Choi, Ki-Sang Hong, Hong Joeng, The Development of Intelligent Robot Using Vision and Speech Recognition System, Department of EE, Postech, 1993, p. 39-44.

Jae-Hun Jung, Yong-Hyun Jung, Jong-Mo Kim, Suck-Gyu Lee, Dal-Hae Lee, Motion Control of Autonomous Mobile Robot With Fuzzy Algorithm, Yeungnam Univ., 1993, p. 362-365.

Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering , 1993, p. 170-177.

A Study on a Basic System Configuration for the PC Interface and the Robot Trajectory Generation, 1993, p. 354-358.

G.T. Yang, S.D. Ahn, S.C. Lee, Tip Position Control of Flexible Robot Arm by Self-Tuning Fuzzy Algorithm, Chonbuk Univ., 1993, p. 213-217.

Jeong Park, Hoe-Young Yoo, The Study of the Method of Position Control for the One-Link Flexible Robot Arm, 1993, p. 57-60.

ASEA Industrial Robot System IRb-60, 1975, p. 1-8.

Robots Take a Hold on Production, 1982, p. 122-129.

M. Peter Heilburn, M.D., J., Preliminary Experience With Brown-Robert-Wells (BRW) Computerized Tomography Stereotaxis Guidance System, Neurourgery, 1983, p. 217-221.

International Machine Intelligence Robot System Users Manual, International Machine Intelligence, 1983.

Orbitran Wafer Handling Robot, Genmark Automation, 1989, p. 2,3,4.

H Kojima, R Toyama, Development of Wall Cleaning Robot, 1992.

L.E. Weiss, "Dynamic Visual Servo Control of Robots: an adaptive image-based approach, Technical Report", Part 2 Carnegie Mellon, 1984.

L.E. Weiss, "Dynamic Visual Servo Control of Robots: an adaptive image-based approach, Technical Report", Part 3 Carnegie Mellon, 1984.

International Search Report and the Written Opinion dated Apr. 17, 2015, issued in corresponding International Patent Application No. PCT/US2014/071400.

Extended European Search Report dated Jul. 28, 2017 issued in European Application No. 14876741.1.

\* cited by examiner

ARTICULATING ROBOTIC PROBES

RELATED APPLICATIONS

This application claims the benefit of U.S. Provisional Application No. 61/921,858, filed Dec. 30, 2013, the content of which is incorporated herein by reference in its entirety.

This application claims the benefit of U.S. Provisional Application No. 62/008,453, filed Jun. 5, 2014, the content of which is incorporated herein by reference in its entirety.

This application is related to U.S. Provisional Application No. 61/406,032, filed Oct. 22, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. patent application Ser. No. 13/880,525, filed Apr. 19, 2013, the content of which is incorporated herein by reference in its entirety.

This application is related to U.S. Provisional Application No. 61/492,578, filed Jun. 2, 2011, the content of which is incorporated herein by reference in its entirety.

This application is related to PCT Application No. PCT/US12/40414, filed Jun. 1, 2012, the content of which is incorporated herein by reference in its entirety.

This application is related to U.S. patent application Ser. No. 14/119,316, filed Nov. 21, 2013, the content of which is incorporated herein by reference in its entirety.

This application is related to U.S. Provisional Application No. 61/412,733, filed Nov. 11, 2010, the content of which is incorporated herein by reference in its entirety.

This application is related to PCT Application No PCT/US2011/060214, filed Nov. 10, 2011, the content of which is incorporated herein by reference in its entirety.

This application is related to U.S. patent application Ser. No. 13/884,407, filed May 9, 2013, the content of which is incorporated herein by reference in its entirety.

This application is related to U.S. Provisional Application No. 61/472,344, filed Apr. 6, 2011, the content of which is incorporated herein by reference in its entirety.

This application is related to PCT Application No. PCT/US12/32279, filed Apr. 5, 2012, the content of which is incorporated herein by reference in its entirety.

This application is related to U.S. patent application Ser. No. 14/008,775, filed Sep. 30, 2013, the content of which is incorporated herein by reference in its entirety.

This application is related to U.S. Provisional Application No. 61/534,032 filed Sep. 13, 2011, the content of which is incorporated herein by reference in its entirety.

This application is related to PCT Application No. PCT/US12/54802, filed Sep. 12, 2012, the content of which is incorporated herein by reference in its entirety.

This application is related to U.S. patent application Ser. No. 14/343,915, filed Mar. 10, 2014, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. patent application Ser. No. 13/812,324, filed Jan. 25, 2013, the content of which is incorporated herein by reference in its entirety.

This application is related to U.S. Provisional Application No. 61/578,582, filed Dec. 21, 2011, the content of which is incorporated herein by reference in its entirety.

This application is related to PCT Application No. PCT/US12/70924, filed Dec. 20, 2012, the content of which is incorporated herein by reference in its entirety.

This application is related to U.S. patent application Ser. No. 14/364,195, filed Jun. 10, 2014, the content of which is incorporated herein by reference in its entirety.

This application is related to U.S. Provisional Application No. 61/681,340, filed Aug. 9, 2012, the content of which is incorporated herein by reference in its entirety.

This application is related to PCT Application No. PCT/US13/54326, filed Aug. 9, 2013, the content of which is incorporated herein by reference in its entirety.

This application is related to U.S. Provisional Application No. 61/751,498, filed Jan. 11, 2013, the content of which is incorporated herein by reference in its entirety.

This application is related to PCT Application No. PCT/US14/01808, filed Jan. 9, 2014, the content of which is incorporated herein by reference in its entirety.

This application is related to U.S. Provisional Application No. 61/656,600, filed Jun. 7, 2012, the content of which is incorporated herein by reference in its entirety.

This application is related to PCT Application No. PCT/US13/43858, filed Jun. 3, 2013, the content of which is incorporated herein by reference in its entirety.

This application is related to U.S. patent application Ser. No. 14/402,224, filed Nov. 19, 2014, the content of which is incorporated herein by reference in its entirety.

This application is related to U.S. Provisional Application No. 61/825,297, filed May 20, 2013, the content of which is incorporated herein by reference in its entirety.

This application is related to PCT Application No. PCT/US13/38701, filed May 20, 2014, the content of which is incorporated herein by reference in its entirety.

This application is related to U.S. Provisional Application No. 61/818,878, filed May 2, 2013, the content of which is incorporated herein by reference in its entirety.

This application is related to PCT Application No. PCT/US14/36571, filed May 2, 2014, the content of which is incorporated herein by reference in its entirety.

This application is related to U.S. Provisional Application No. 61/909,605, filed Nov. 27, 2013, the content of which is incorporated herein by reference in its entirety.

This application is related to U.S. Provisional Application No. 62/052,736, filed Sep. 19, 2014, the content of which is incorporated herein by reference in its entirety.

This application is related to PCT Application No. PCT/US14/67091, filed Nov. 24, 2014, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

TECHNICAL FIELD

The present inventive concepts generally relate to the field of surgical instruments, and more particularly, to articulated probe assemblies.

BACKGROUND

As less invasive medical techniques and procedures become more widespread, medical professionals such as surgeons may require articulating surgical tools, such as endoscopes, to perform such less invasive medical techniques and procedures that access interior regions of the body via a body orifice such as the mouth.

SUMMARY

In one aspect, provided is an articulated probe assembly, comprising a base; an outer support rod extending through the base; an articulating control portion at a proximal end of the outer support rod; and a steerable portion comprising a plurality of outer links coupled to a distal end of the outer support rod. The steerable portion is manipulated in response to the articulating control portion.

In some embodiments, the articulating control portion is above the base and the steerable portion is below the base.

In some embodiments, the articulating control portion comprises a plurality of second outer links that articulate relative to each other for controlling an articulation of the outer links of the steerable portion.

In some embodiments, the articulating control portion comprises a plurality of channels, and the support rod comprises a plurality of channels that are aligned with the channels of the control portion, each support rod channel and corresponding control portion channel receiving a steering cable, the steering cables constructed and arranged to control a motion of the steerable portion in response to an articulation of the second outer links relative to each other.

In some embodiments, the articulating control portion comprises an articulating element that articulates the steerable portion relative to the control portion according to at least one degree of freedom.

In some embodiments, the articulating element includes at least one of a universal joint, a ball joint, a spherical joint, or a hinged joint.

In some embodiments, the at least one degree of freedom includes an articulation selected from the group consisting of: steering in a single plane; rotation about a single axis; linear translation along a single axis; and combinations thereof.

In some embodiments, the articulated probe assembly further comprises an inner rod that extends through at least a portion of the outer support rod and at least a portion of the steerable portion.

In some embodiments, articulation of the steerable portion is controlled by a location of the inner rod.

In some embodiments, when the inner rod is at its highest point, the steerable portion has a greatest range of motion.

In some embodiments, the articulated probe assembly further comprises a translation assembly that translates the inner rod, wherein the inner rod translates via the translation assembly vertically within the outer support rod.

In some embodiments, when the translation assembly moves linearly along the outer support rod, a number of outer links of the steerable portion that can articulate is changed.

In some embodiments, the base comprises a height adjustment gear and the outer support rod comprises a linear gear that engages with the height adjustment gear for changing a height of the outer support rod, which in turn changes a height of the steerable portion relative to the base.

In some embodiments, the plurality of outer links of the steerable portion includes a distal link, the distal link including at least one exit port from which a tool can extend for insertion into a surrounding environment.

In some embodiments, the surrounding environment is selected from the group consisting of: the esophagus, the gastrointestinal tract, the pericardial space, the peritoneal space, or combinations thereof.

In some embodiments, the articulated probe assembly further comprises at least one side channel coupled to the distal link for receiving one or more tools.

In some embodiments, the at least one side channel is configured to perform one or more of: slidingly receiving a shaft of a tool, guiding the shaft of a tool, providing a supporting force for a tool, or combinations thereof.

In some embodiments, the articulated probe assembly further comprises a handle that articulates the control portion, which in turn articulates the steerable portion.

In some embodiments, the articulated probe assembly further comprises a plurality of steering cables operably connected to the handle, wherein movement of the handle applies tension to the steering cables which in turn articulates the steerable portion.

In some embodiments, the steering cables extend from channels in the control portion, through matching channels in the support rod, through channels in the steerable portion, and terminating at a distal link of the outer links.

In some embodiments, the articulated probe assembly further comprises a cable tensioning assembly operably connecting the steering cables to the handle, wherein the cable tensioning assembly is constructed and arranged to adjust the tension in one or more of the steering cables.

In some embodiments, the cable tensioning assembly is constructed and arranged to adjust tension in multiple cables to transition the steerable portion between an articulable state and a locked state.

In some embodiments, the cable tensioning assembly is constructed and arranged to increase the tension applied to each and all of the steering cables to cause the steerable portion to transition from the articulable state to the locked state.

In some embodiments, the cable tensioning assembly is biased such that the steerable portion is in the locked state.

In some embodiments, the cable tensioning assembly comprises a button constructed and arranged to decrease the tension applied to at least one steering cable to cause the steerable portion to transition from the locked state to the articulable state.

In some embodiments, the cable tensioning assembly includes a tensioning plate that is slidingly received by a channel within the handle.

In some embodiments, the steering cables are attached to the tensioning plate via one or more attachment screws, which can be individually adjusted for individual tensioning of the steering cables with respect to the tensioning plate.

In some embodiments, the articulated probe assembly further comprises a tensioning screw extending through the handle to the tensioning plate, the tensioning screw slidingly receiving a spring, is slidingly received by the handle, and rotatably engages the tensioning plate, wherein the tensioning screw is rotated to adjust a tension in the steering cables.

In some embodiments, a tightening of the tensioning screw compresses the spring and applies a force to the tensioning plate, and in turn applies a locking force to the steering cables.

In some embodiments, a depression of the tensioning screw further compresses the spring, relieving tension on the steering cables, and allowing articulation of the control portion and a manipulation of the steering portion.

In some embodiments, releasing the tensioning screw applies a spring force to the tensioning plate, locking the articulated position.

In some embodiments, the base is coupled to a support arm.

In some embodiments, the support arm is coupled to at least one of a floor, a table, or other supporting object.

In some embodiments, the articulated probe assembly further comprises an inner rod slidingly positioned within the outer support rod and a translation assembly, wherein the steerable portion comprises an articulation region, and wherein the translation assembly translates the inner rod to adjust a range of motion of the articulation region of the steerable portion.

In some embodiments, the translation assembly comprises a collar that is slidingly received by the outer support rod.

In some embodiments, the transition assembly further comprises a gear and at least one knob operably couples to the gear.

In some embodiments, the collar engages the gear with a linear gear of the outer support rod.

In some embodiments, a rotation of the at least one knob translates the collar along the outer support rod.

In some embodiments, the outer support rod comprises a slot and the translation assembly comprises a connecting element that is fixedly attached to the collar and the inner rod, passing through the slot, such that the inner rod translates with the collar.

In some embodiments, the outer support rod comprises a set of threads arranged in a helical manner about the outer support rod, wherein the collar includes a set of inner threads at a hole of the collar through which the outer support rod is positioned, and wherein the inner threads of the collar communicate with the threads of the outer support rod such that a rotation of the outer rod causes the outer rod to travel linearly.

In some embodiments, the articulated probe assembly further comprises a tool support assembly, the tool support assembly comprising at least one support rod with a proximal end into which a tool can be inserted.

In some embodiments, the at least one support rod is coupled to the base.

In some embodiments, the at least one support rod comprises two support rods and wherein the articulated probe assembly comprises a dogbone connector coupled between the two support rods.

In some embodiments, the articulated probe assembly further comprises at least one flexible tube positioned in a side channel of a distal link of the outer links and extending along the steerable portion, for guiding a tool extending from the proximal end of the outer support rod to the distal link.

In some embodiments, the at least one support rod comprises a first support rod having a proximal end and a second support rod having a proximal end, and wherein the at least one flexible tube comprises a first flexible tube positioned on a first side channel of the distal link and extending along the steerable portion, for guiding a first tool extending from the first support rod proximal end, and a second flexible tube positioned on a second side channel of the distal link and extending along the steerable portion, for guiding a second tool extending from the second support rod proximal end.

In some embodiments, the outer support rod comprises a set of threads arranged in a helical manner about the outer support rod, wherein the base includes a set of inner threads at a hole of the base through which the outer support rod is positioned, and wherein the inner threads of the base communicate with the threads of the outer support rod such that a rotation of the outer support rod causes the outer support rod to travel linearly relative to the base.

In some embodiments, a method is provided for performing a medical procedure using the articulated probe assembly.

In another aspect provided is an articulated probe assembly, comprising: a steerable portion comprising a plurality of outer links for articulating relative to each other according to a predetermined range of motion; and an advancement rod extending through at least a portion of the steerable portion. The range of motion of the steerable portion is controlled by a position of the advancement rod relative to the steerable portion.

In some embodiments, the articulated probe assembly further comprises a translation assembly that translates the advancement rod, wherein the advancement rod controls a range of motion of the steerable portion in response to a location of the translation assembly.

In some embodiments, when the advancement rod is at its highest point, the steerable portion has a greatest range of motion.

In some embodiments, the articulated probe assembly further comprises a base and an articulating control portion, wherein the articulating control portion is above the base and the steerable portion is below the base.

In some embodiments, the articulating control portion comprises a plurality of second outer links that articulate relative to each other for controlling an articulation of the outer links of the steerable portion.

In some embodiments, the articulating control portion comprises an articulating element that articulates the steerable portion relative to the control portion according to at least one degree of freedom.

In some embodiments, the articulating element includes at least one of a universal joint, a ball joint, a spherical joint, or a hinged joint.

In some embodiments, the at least one degree of freedom includes an articulation selected from the group consisting of: steering in a single plane; rotation about a single axis; linear translation along a single axis; and combinations thereof.

In some embodiments, the articulated probe assembly further comprises a handle that articulates the control portion, which in turn articulates the steerable portion.

In some embodiments, the articulated probe assembly further comprises a plurality of steering cables operably connected to the handle, wherein movement of the handle applies tension to the steering cables which in turn articulates the steerable portion.

In some embodiments, the steering cables extend from channels in the control portion, through matching channels in the support rod, through channels in the steerable portion, and terminating at a distal link of the outer links.

In some embodiments, the articulated probe assembly further comprises a cable tensioning assembly operably connecting the steering cables to the handle, wherein the cable tensioning assembly is constructed and arranged to adjust the tension in one or more of the steering cables.

In some embodiments, the cable tensioning assembly is constructed and arranged to adjust tension in multiple cables to transition the steerable portion between an articulable state and a locked state.

In some embodiments, the cable tensioning assembly includes a tensioning plate that is slidingly received by a channel within the handle.

In some embodiments, the steering cables are attached to the tensioning plate via one or more attachment screws, which can be individually adjusted for individual tensioning of the steering cables with respect to the tensioning plate.

In some embodiments, the articulated probe assembly further comprises a translation assembly that translates the advancement rod in a linear direction relative to a direction of extension of the probe assembly, which in turn changes a number of outer links of the steerable portion that can articulate.

In some embodiments, the articulated probe assembly further comprises a height adjustment gear and an outer support rod that comprises a linear gear that engages with the height adjustment gear for changing a height of the outer support rod, which in turn changes a height of the steerable portion.

In some embodiments, the plurality of outer links of the steerable portion includes a distal link, the distal link including at least one exit port from which a tool can extend for insertion into a surrounding environment.

In some embodiments, the surrounding environment is selected from the group consisting of: the esophagus, the gastrointestinal tract, the pericardial space, the peritoneal space, or combinations thereof.

In some embodiments, the articulated probe assembly further comprises at least one side channel coupled to the distal link for receiving one or more tools.

In some embodiments, the at least one side channel is configured to perform one or more of: slidingly receiving a shaft of a tool, guiding the shaft of a tool, providing a supporting force for a tool, or combinations thereof.

In some embodiments, the base is coupled to a support arm.

In some embodiments, the support arm is coupled to at least one of a floor, a table, or other supporting object.

In some embodiments, the advancement rod is slidingly positioned within an outer support rod and a translation assembly, wherein the steerable portion comprises an articulation region, and wherein the translation assembly translates the advancement rod to adjust a range of motion of the articulation region of the steerable portion.

In some embodiments, the translation assembly comprises a collar that is slidingly received by the outer support rod.

In some embodiments, the transition assembly further comprises a gear and at least one knob operably couples to the gear.

In some embodiments, a rotation of the at least one knob translates the collar along the outer support rod.

In some embodiments, the outer support rod comprises a slot and the translation assembly comprises a connecting element that is fixedly attached to the collar and the inner rod, passing through the slot, such that the inner rod translates with the collar.

In some embodiments, the outer support rod comprises a set of threads arranged in a helical manner about the outer support rod, wherein the collar includes a set of inner threads at a hole of the collar through which the outer support rod is positioned, and wherein the inner threads of the collar communicate with the threads of the outer support rod such that a rotation of the outer rod causes the outer rod to travel linearly.

In some embodiments, the outer support rod comprises a set of threads arranged in a helical manner about the outer support rod, wherein the base includes a set of inner threads at a hole of the base through which the outer support rod is positioned, and wherein the inner threads of the base communicate with the threads of the outer support rod such that a rotation of the outer rod causes the outer rod to travel linearly relative to the base.

In some embodiments, the articulated probe assembly further comprises a tool support assembly, the tool support assembly comprising at least one support rod with a proximal end into which a tool can be inserted.

In some embodiments, the at least one support rod is coupled to the base.

In some embodiments, the at least one support rod comprises two support rods and wherein the articulated probe assembly comprises a dogbone connector coupled between the two support rods.

In some embodiments, the articulated probe assembly further comprises at least one flexible tube positioned in a side channel of a distal link of the outer links and extending along the steerable portion, for guiding a tool extending to the distal link.

In some embodiments, the at least one support rod comprises a first support rod having a proximal end and a second support rod having a proximal end, and wherein the at least one flexible tube comprises a first flexible tube positioned on a first side channel of the distal link and extending along the steerable portion, for guiding a first tool extending from the first support rod proximal end, and a second flexible tube positioned on a second side channel of the distal link and extending along the steerable portion, for guiding a second tool extending from the second support rod proximal end.

In some embodiments, a method is provided for performing a medical procedure using the articulated probe assembly.

In some embodiments, a system is provided as described in reference to the figures.

In some embodiments, a method is provided for performing a medical procedure as described in reference to the figures.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same elements throughout the different views. The drawings are not necessarily to scale, emphasis instead being placed upon illustrating the principles of the preferred embodiments.

DETAILED DESCRIPTION OF EMBODIMENTS

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

Figure 1:
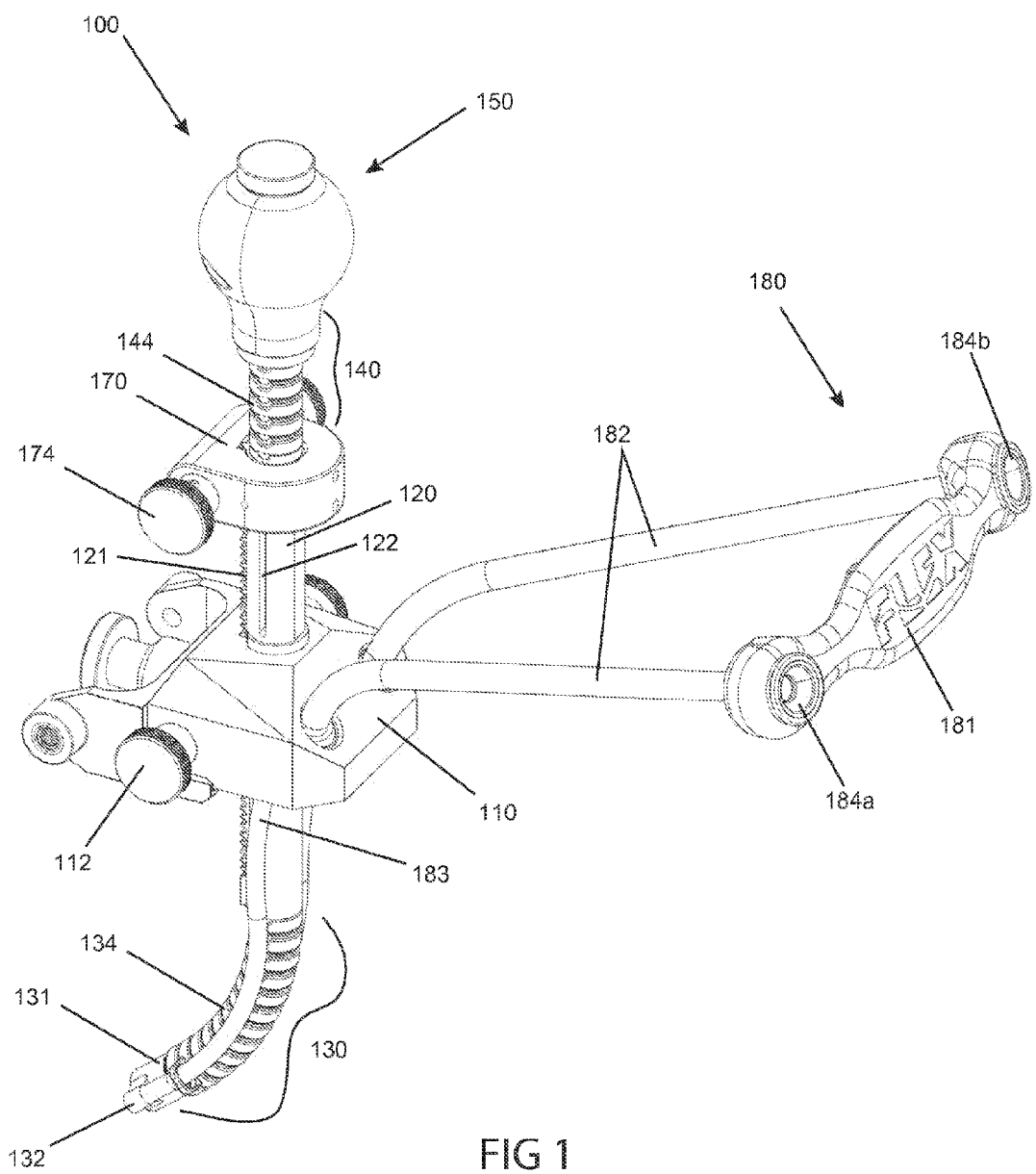
FIG. 1 is an isometric view of an articulated probe assembly, in accordance with embodiments of the present inventive concepts.

FIG. 1 is an isometric view of an articulated probe assembly 100, in accordance with embodiments of the present inventive concepts.

The probe assembly 100 comprises a base 110 and an outer support rod 120 that extends through the base 110. The probe assembly 100 also comprises an articulating control portion 140 at a proximal end of the outer support rod 120 and a steerable portion 130 coupled to a distal end of the outer support rod 120. The articulating control portion 140 is above the base 110 and the steerable portion is below the base 110. The steerable portion 130 can be manipulated in response to an articulation of the control portion 140, described in detail below.

The probe assembly 100 can comprise a handle 150 that articulates the control portion 140, which in turn articulates the steerable portion 130. The articulating control portion 140 can further comprise a plurality of outer links 144 that articulate relative to each other, for example, in response to a movement of the handle 150, for controlling an articulation of one or more outer links 134 of the steerable portion 130. The outer links 144 of the control portion 140 can be configured similarly to the outer links 134 of the steerable portion 130. The outer links 134, 144 can be made out of virtually any material, including plastic or other magnetic resonance imaging compatible material. As described herein, a plurality of steering cables can extend through the outer links 134, 144, which when pulled in response to a movement of the handle 150 can permit the outer links 134 of the steerable portion to articulate relative to each other.

Figure 2:
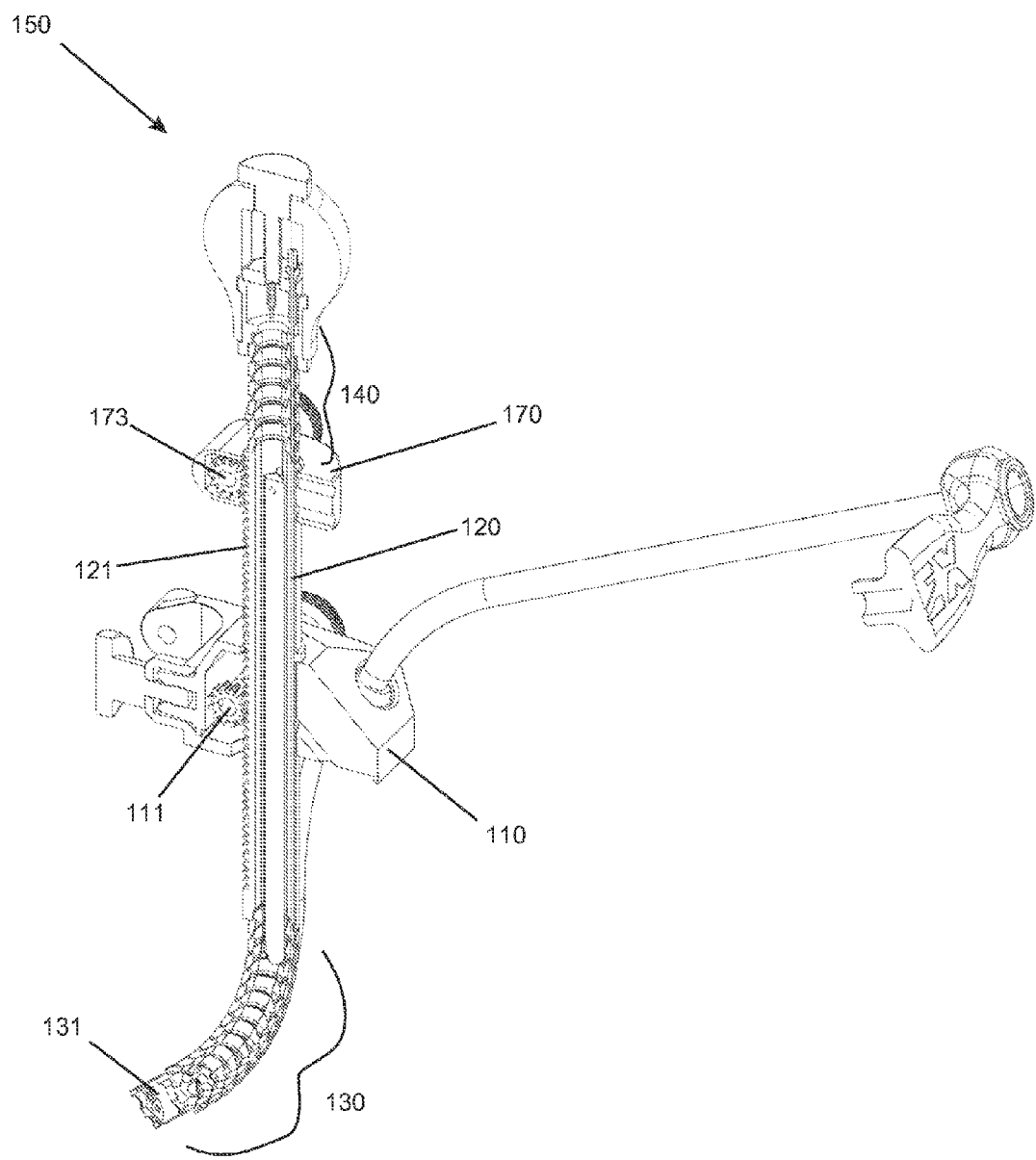
FIG. 2 is a cutaway view of the articulated probe assembly of FIG. 1, in accordance with embodiments of the present inventive concepts.
Figure 6:
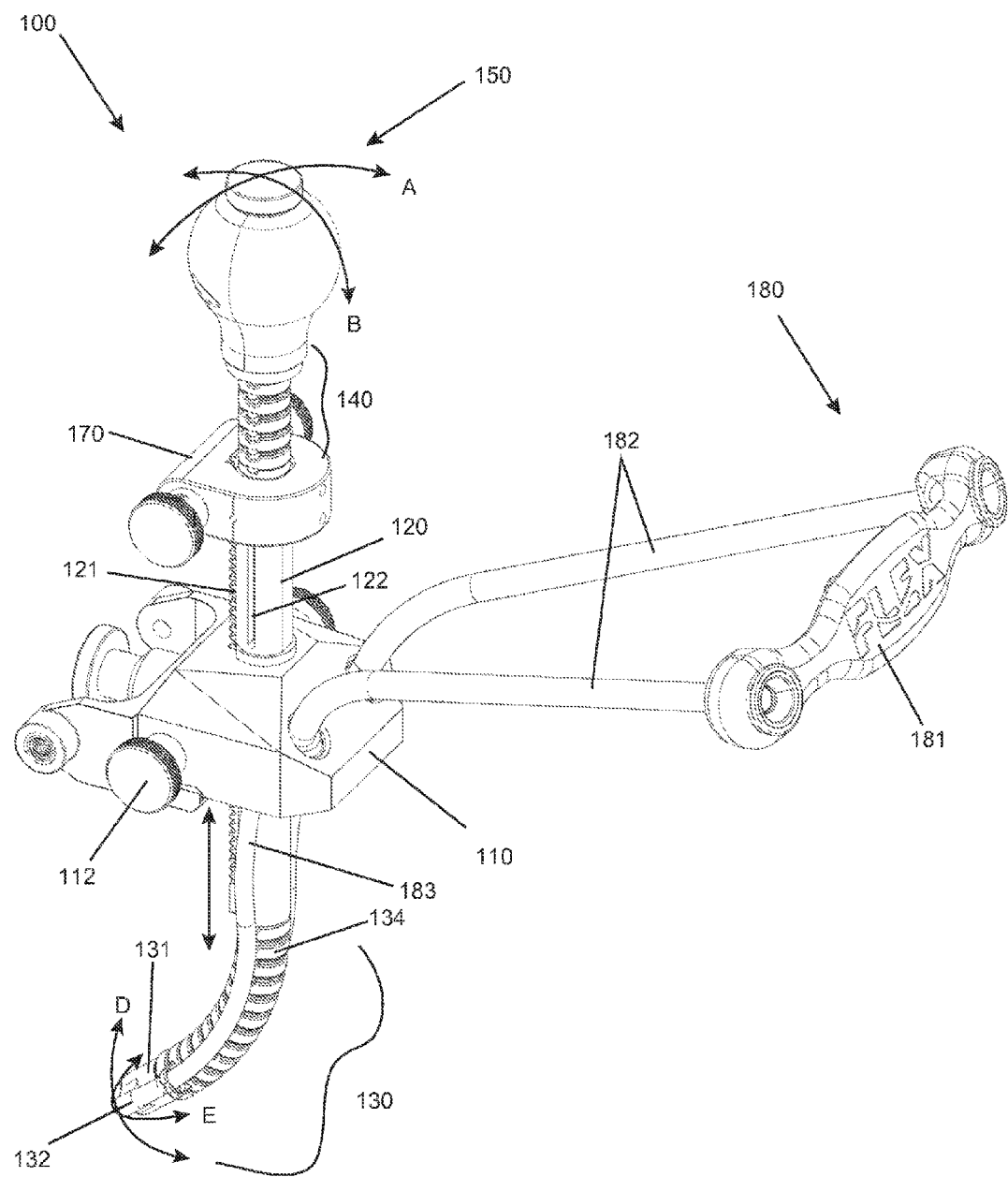
FIG. 6 is an isometric view of an articulated probe assembly of FIGS. 1-5, including arrows illustrating various articulations of the probe assembly, in accordance with embodiments of the present inventive concepts.

As shown in FIG. 2, the base 110 can comprise a height adjustment gear 111. The outer, support rod 120 can comprise a linear gear 121, or ratchet gear, that engages with the height adjustment gear 111. A height adjustment knob 112 can be directly or indirectly in communication with the height adjustment gear 111. When the adjustment knob 112 is turned, the height adjustment gear 111 rotates and in doing so engages with the linear gear 121 for changing a height of the outer support rod 120 in a linear direction with a single degree of freedom, for example, in a direction C as shown in FIG. 6. A corresponding movement of the outer support rod 120 in turn changes a height of the steerable portion 130 relative to the base 110, shown by arrow C in FIG. 6, for example, allowing the steering portion 130 to move up and down with respect to base 110 (e.g. to allow steering portion 130 to move up and down with respect to a patient's mouth, throat, esophagus, or other orifice or internal space).

The base 110 can be directly or indirectly coupled to a support arm (not shown), such as via an adapter, which in turn can be coupled to a fixed object such as an operating table, floor, or other supporting object. The support arm can be configured to provide a stabilizing force for the probe assembly 100, such that the height adjustment knob 112 and adjustment gear 111 can advance or retract a distal link 131 of the steerable outer links 134 with respect to their positions relative to the base 110, and therefore accommodate a location of the steerable portion 130 into or out of a patient orifice, e.g., deeper or shallower in the throat.

In another embodiment, the probe assembly 100 does not include a adjustment knob 112 and corresponding adjustment gear 111. Instead, the outer rod 120 comprises a set of threads arranged in a helical manner about the outer rod 120. The base 110 includes a set of inner threads at a hole of the base 110 through which the outer rod 120 is positioned. The threads of the base 110 can mate or otherwise align with the threads of the outer rod 120 in a manner such that a rotation of the outer rod 120 causes the outer rod 120 to travel linearly relative to the base, for example, an up and down motion.

Figure 5:
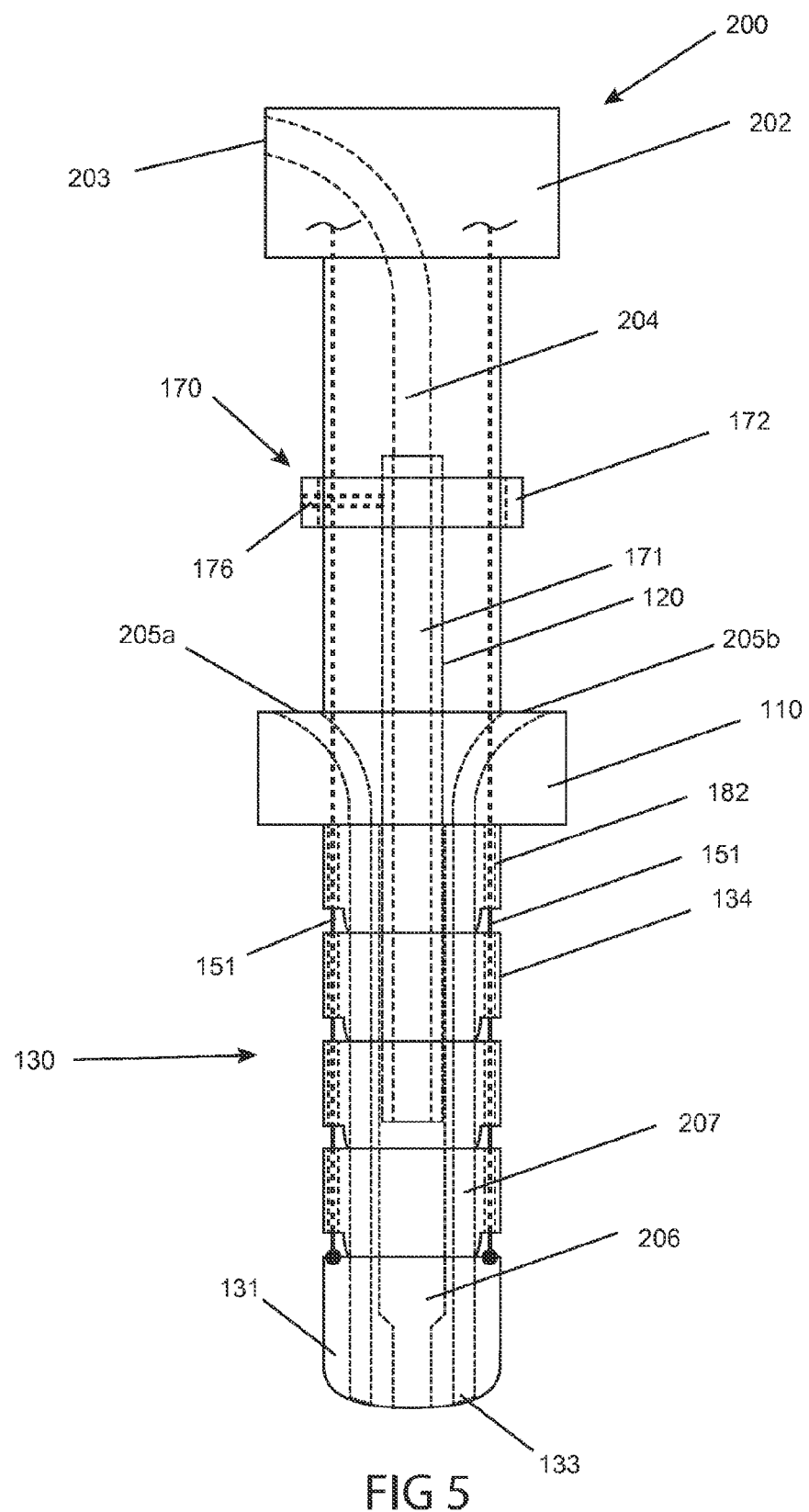
FIG. 5 is a cross-sectional view of an articulated probe assembly, in accordance with embodiments of the present inventive concepts.

The distal link 131 can include at least one opening or exit port 133, as shown in FIG. 5 herebelow, from which a tool can slidingly extend for insertion into a surrounding environment. The surrounding environment can include a region of a patient's body, such as the esophagus, the gastrointestinal tract, the pericardial space, the peritoneal space, and/or combinations thereof. At least one side channel 132, also referred to as a tool side port or tool guide, can be coupled to, or integrally extend from, the distal link 131, for example, formed in a flange of the outer distal link 131 for receiving one or more tools. In particular, the side channel 132 can be configured to slidingly receive a shaft of a tool, guide the shaft of a tool, provide a supporting force for a tool, or combinations thereof. Examples of tools can include but not be limited to a claw, scissors, a cutter, a knife, an ablator, a cauterizer, a drug delivery apparatus, a radiation source, a laser emitter, an energy delivery element such as a RF electrode, a sensor such as a pressure sensor or a blood sensor, a camera, a magnet, a heating element, a cryogenic element, or a combination thereof. Accordingly, a single operator can operate one or more of the tools at the probe assembly 100, for example, from a single operator location. Alternatively, one operator can operate one or more tools, and another operator can operate the remaining tools at the probe assembly 100.

The probe assembly can further comprise a tool support assembly 180. The tool support assembly 180 can comprise at least one support tube 182, also referred to as a tool support or rod, which can be coupled to the base 110. Each tube 182 can include a proximal end into which a tool can be inserted. A connector 181, commonly referred to as a "dogbone connector", can be coupled between proximal ends of two support tubes 182, for example, described with reference to U.S. Provisional Application No. PCT/US13/54326, filed Aug. 9, 2013, incorporated by reference above. The connector 181 can be constructed and arranged to maintain a relative position between the support tubes 182. The connector 181 can be removed from the support tubes 182 and replaced with a different connector having different parameters, configuration, etc. Accordingly, in some embodiments, the tool support assembly 180 is used with two or more different second assemblies, depending on the medical procedure.

The connector 181 comprises a first opening 184a and a second opening 184b (generally, 184), each constructed and arranged to operably engage a tube 182. At least one of the first opening 184a or the second opening 184b can comprise a funnel-shaped opening. An uninterrupted tool path can extend from an opening 184 through a tube 182, the base 110, and at least one flexible guide tube 183 at an opposite side of the base 110 to a side channel 132 at a distal outer link 131 of the steerable portion 130. The guide tube 183 can extend along a longitudinal axis of the steerable portion 130. The guide tube 183 is configured to guide or otherwise provide a support for a tool, so that the tool can be guided from the proximal end of the outer support rod 120 to the distal outer link 131, for example, into the tool side channel 132 at the distal outer link 131. Thus, the probe assembly 100 can facilitate the introduction of tools passed through the side channel 132 and/or working channels extending through an interior of the outer links 144, for example, shown at FIG. 5. In some embodiments, the support tubes 182 comprise a first support tube with a proximal end and a second support tube with a proximal end. Here, the flexible guide tube 183 comprises a first flexible tube positioned on a first side channel of the distal link 131 and extending along the steerable portion, for guiding a first tool extending from the first support tube 182, and a second flexible tube positioned on a second side channel of the distal link 131 and extending along the steerable portion 130, for guiding a second tool extending from the second support tube 182.

Figure 3:
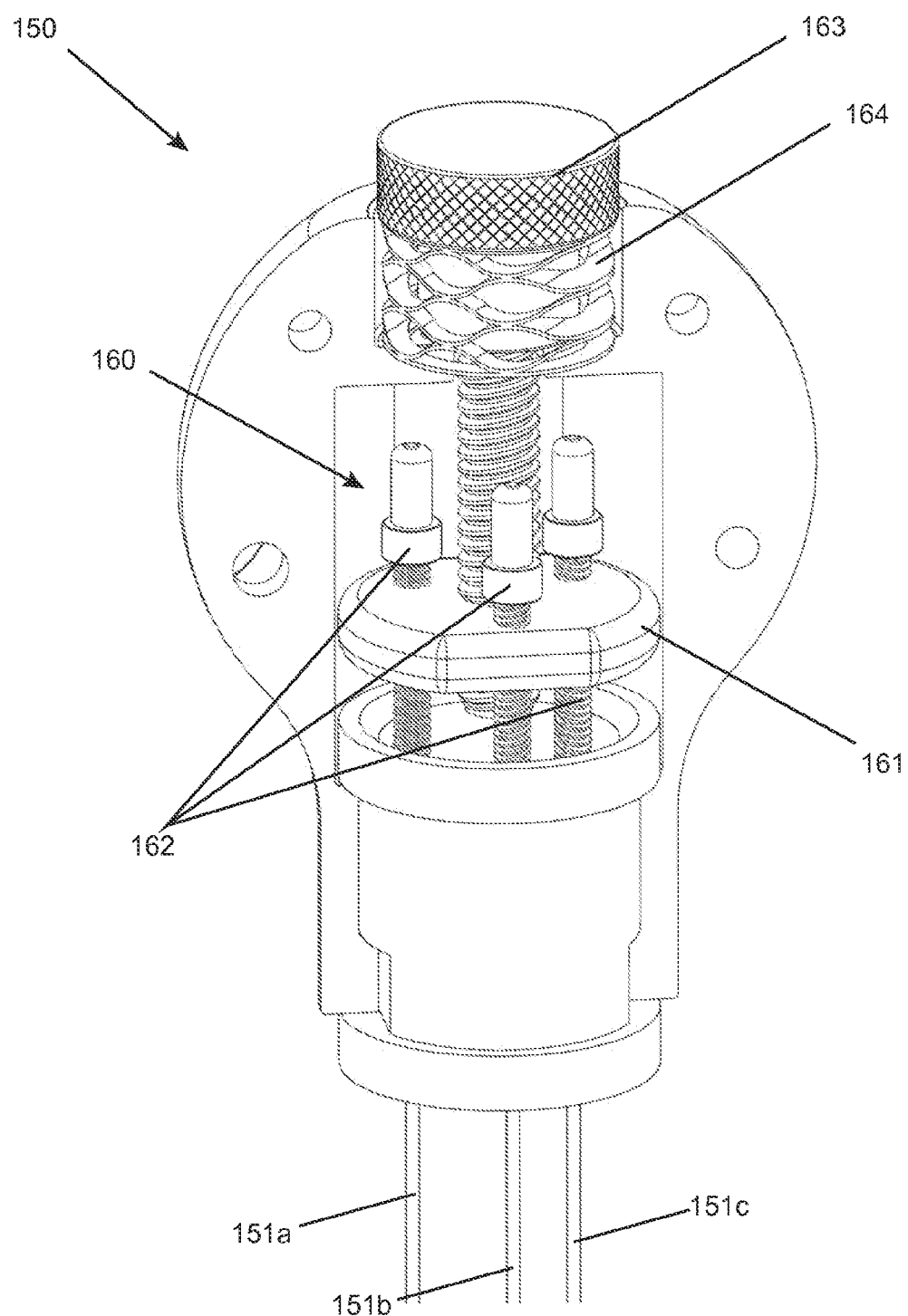
FIG. 3 is a close-up cutaway view of the probe assembly handle of FIGS. 1 and 2, in accordance with embodiments of the present inventive concepts.

FIG. 3 is a close-up cutaway side view of the probe assembly handle 150 of FIGS. 1 and 2, in accordance with embodiments of the present inventive concepts.

A plurality of steering cables 151a-151c (generally, 151) are operably connected to the handle 150, and are constructed and arranged to extend through the control portion 140, the translation assembly 170, and the base 110, respectively, to the steerable portion 130. For example, the steering cables 151 can extend from channels in the control portion 140, through matching, or aligned, channels in the support rod 120, through support tube 182 in the steerable portion 130 (see FIG. 5), and terminate at the distal link 131 of the outer links 134 of the steerable portion 130. Accordingly, a movement of the handle 150 applies tension to one or more of the steering cables 151, which in turn articulates the steerable portion 130. The steering cables 151 can be constructed and arranged to control a motion of the steerable portion 130 in response to an articulation of the second outer links 144 of the control portion 140 relative to each other. For example, the steering cables 151 can articulate the outer links 134 relative to each other during manipulation of the handle 150. In another example, the steering cables 151 can selectively apply tension to cause the steerable portion 130 to transition between a locked state and an articulatable state.

A cable tensioning assembly 160 can be positioned at the handle 150 for operably connecting the steering cables 151 to the handle 150. The cable tensioning assembly 160 can be constructed and arranged to adjust the tension in one or more of the steering cables 151 individually. Additionally or alternatively, the cable tensioning assembly 160 can be constructed and arranged to adjust tension in multiple steering cables 151 to transition the steerable portion 130 between an articulable state and a locked state. For example, the cable tensioning assembly 160 can be constructed and arranged to increase the tension applied to each and all of the steering cables 151 to cause the steerable portion 130 to transition from the articulable state to the locked state, whereby the steerable portion 130 is locked in a fixed position so that some or all of the links of the steerable portion 130 do not articulate relative to each other. The cable tensioning assembly 160 can be biased such that the steerable portion 130 is in the locked state, such as via a spring 164.

The cable tensioning assembly 160 can include a tensioning plate 161 that is positioned in the handle 150, more specifically, slidingly received by a channel within the handle 150. The steering cables 151 can be attached to the tensioning plate 161 via one or more attachment screws 162, which can be individually adjusted for individual tensioning of the steering cables 151 with respect to the tensioning plate 161 (i.e. tension between tensioning plate 161 and a region where the steering cables 151 terminate at distal link 131). A tensioning screw 163 can extend through a surface of the handle 150 to the tensioning plate 161. The tensioning screw 163 can slidingly receive the spring 164. The tensioning screw 163 can be slidingly received by the handle 150, and rotatably engage, for example, screw into, the tensioning plate 161. The tensioning screw 163 can be rotated to adjust a tension in the steering cables 151 attached to the tensioning screw 163. A tightening of the tensioning screw 163 compresses the spring 164 between at least a portion of handle 150 and at least a portion of screw 163. Spring 164 applies a force to screw 163, and in turn to the tensioning plate 161, and in turn applies a locking force to the steering cables 151. Spring 164 biases probe assembly 100 in a locked or otherwise non articulable state. A depression of the tensioning screw 163 against spring 164 linearly translates tensioning plate 161 thereby relieving the locking tension on steering cables 151, and allowing an articulation of the control portion 140 and a manipulation of the steering portion 130. Releasing the tensioning screw 163 reapplies the spring force to the tensioning plate 161 thereby locking the articulated position.

Figure 4:
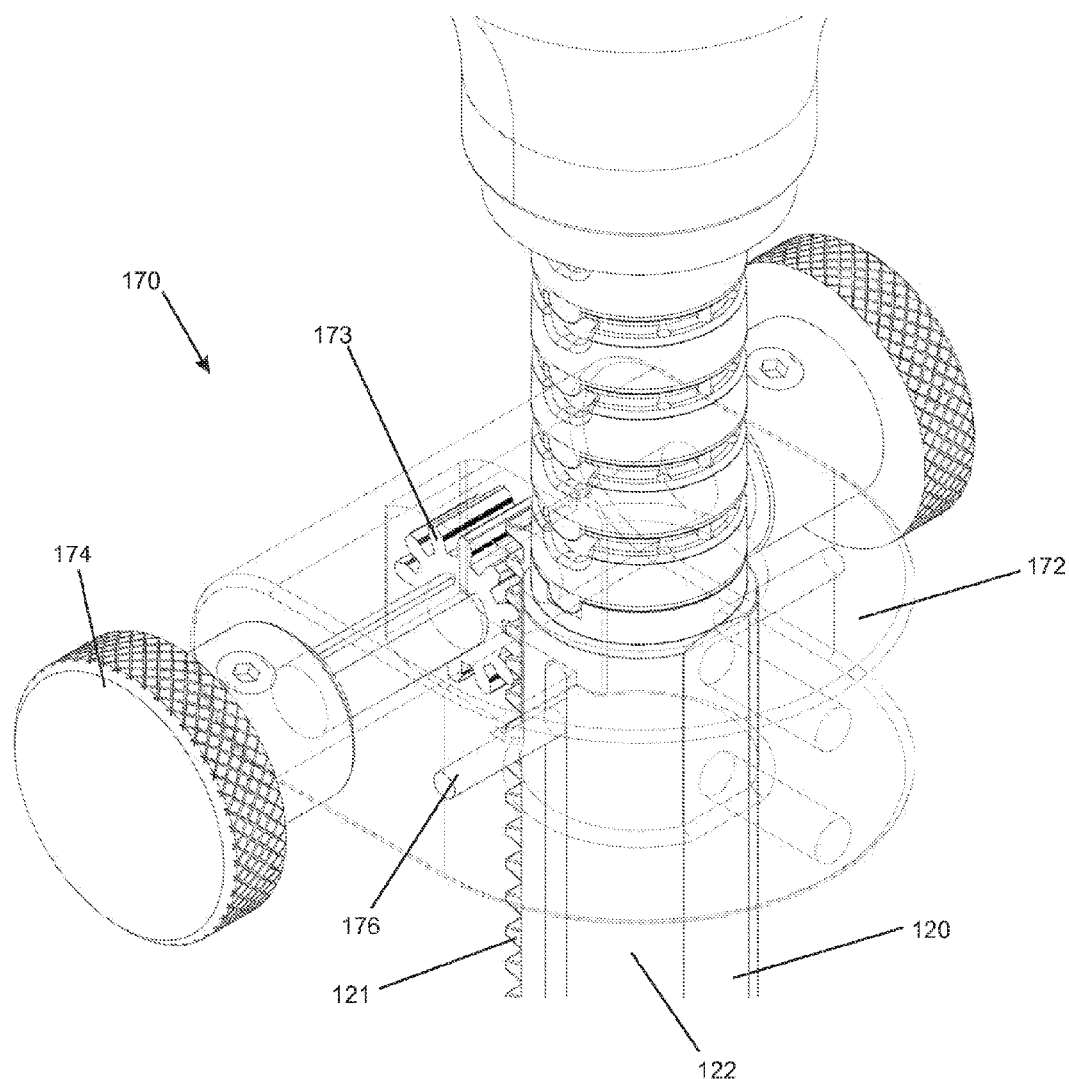
FIG. 4 is a close-up view of the articulated probe assembly of FIGS. 1-3, illustrating interior elements of a translation assembly, in accordance with embodiments of the present inventive concepts.

FIG. 4 is a close-up view of the articulated probe assembly 100 of FIGS. 1-3, illustrating interior elements of a translation assembly 170, in accordance with embodiments of the present inventive concepts.

As shown in FIG. 4, the probe assembly 100 can comprise an inner rod 171 slidingly positioned within the outer support rod 120 and the translation assembly 170, that extends to at least a portion of the steerable portion 130. The translation assembly 170 can translate the inner rod 171 to adjust a range of motion of an articulation region of the steerable portion 130. When the translation assembly 170 moves linearly along the outer support rod 120, a number of outer links 134 of the steerable portion 130 that can articulate is changed, for example, increased or decreased accordingly with an increased or decreased range of motion of the steerable portion 130. Thus, an articulation of the steerable portion 130 is controlled by a location of the inner rod 171. When the inner rod 171 is at its highest point along a direction of extension of the probe assembly 100, the steerable portion 130 has a greatest range of motion. Other the other hand, the range of motion becomes more restricted when the inner rod 171 is at points lower than the highest point along the direction of extension of the probe assembly 100.

The translation assembly 170 can comprise a collar 172 that is slidingly received by the outer support rod 120. The transition assembly can further comprise at least one gear 173 and a knob 174 operably coupled to the gear 173. The collar 172 engages the gear 173 with the linear gear 121 of the outer support rod 120. The outer support rod 120 can comprise a slot or groove 122 that extends along a direction of extension of at least a portion of the outer support rod 120 (also shown in FIGS. 1 and 6). The translation assembly 170 can comprise a connecting element 176 such as a pin or the like that engages the collar 172 with the inner rod 171. The connecting element 176 extends from the collar 172 to the slot, and can translate linearly in the slot. Accordingly, the inner rod 171 translates with the collar 172 along the outer support rod 120 when the knob 174 is rotated. Inner rod 171 is positioned within at least a portion of steerable portion 130, and prevents the articulation of any surrounding links 134 with respect to each other. For example, when inner rod 171 is positioned approximately half way within steerable portion 130, approximately one half of links 134 are prevented from rotating with respect to each other, limiting the possible angle of articulation of steerable portion 130 by approximately half. As shown in FIG. 2, translation assembly 170 is in its highest location, such that inner rod 171 limits the articulation of portion 130 to a minimum articulation or no articulation.

In an alternative embodiment, the translation assembly 170 does not include a knob 174 and corresponding gear 173. Instead, the outer rod 120 comprises a set of threads arranged in a helical manner about the outer rod 120. The collar 172 includes a set of inner threads at a hole of the collar 172 through which the outer rod 120 can be positioned. The threads of the collar 172 can mate with the threads of the outer rod 120 in a manner such that a rotation of the collar 172 causes the inner rod 171 to travel up and down.

FIG. 5 is another cross-sectional view of an articulated probe assembly 200, in accordance with embodiments of the present inventive concepts. The probe assembly 200 can include elements that are the same as or similar to those of the articulated probe assembly 100 of FIGS. 1-4. Details of such elements are not repeated for brevity. The probe assembly 200 can include elements that are included in, but not described with respect to, FIGS. 1-4.

The probe assembly 200 can include a steering box 202, also referred to as an articulating element, having at least one working channel 203 extending therethrough that communicates with an inner core of the probe assembly 200. The inner core can include a working channel 204 extending through an inner rod 171 and/or an outer support rod 120. Each outer link 134, including the distal outer link 131, of the steerable portion 130 can include a working channel 206, for receiving the inner rod 171 and any tool that may extend through the working channel 204 extending through the inner rod 171. The steering box 202 can control the probe assembly 200. Steering box 202 can include but not be limited to at least one of a universal joint, a ball joint, a spherical joint, or a hinged joint, and/or can include one or more electromechanical mechanisms constructed and arranged to manipulate the tension in steering cables 151. Steering box 202 can comprise a feeding mechanism similar to the feeder mechanism in applicant's co-pending U.S. patent application Ser. No. 13/884,407, filed May 9, 2013, the contents of which is incorporated herein by reference in its entirety.

In some embodiments, the articulating probe assembly 200 articulates the steerable portion 130 with at least one degree of freedom. A degree of freedom can include but not be limited to articulation in a single plane, rotation about an axis, linear translation along an axis, and combinations of these.

The base 110 can comprise at least one working channel 205a, 205b (generally, 205), which, like the working channel 203 of the steering box 202, can receive a tool. Each working channel 205 of the base 110 can be aligned with a working channel 207 extending through each steerable portion outer link 134 to the distal outer link 131, from where the tool can exit.

FIG. 6 is an isometric view of an articulated probe assembly 100, including arrows illustrating various articulations of the probe assembly, in accordance with embodiments of the present inventive concepts.

As described herein, the handle 150 is constructed and arranged to allow operator manipulation of the steerable portion 130. In doing so, the handle 150 can articulate in an A direction and/or a B direction, resulting in a movement of the steerable portion 130 in a D direction and/or E direction, and/or other curvilinear direction, which can include pivotal, rotational, lateral, and/or other movements according to one or more degrees of freedom. As also described herein, a movement of the translation assembly 170 linearly with respect to the outer support rod 120 can result in a controlled articulation of the steerable portion 130 by limiting the number of outer links 134 that can be articulated in the D and/or E directions. In some embodiments, the articulated probe assembly 100 can be part of a system that includes one or more human interface devices (HIDs) and/or a controller, for example, described in PCT Application No. PCT/US13/54326, filed Aug. 9, 2013 incorporated by reference above. The HIDs can be constructed and arranged to manipulate elements of the articulated probe assembly 100, such as tool supports, tools extending through the tool supports, one or more links, and so on. One or more operators may control the probe assembly 100 via a HID to steer, advance, retract, or otherwise control the functions and movement of the probe assembly 100 via commands sent to/from the controller. An HID may include but not be limited to a haptic controller, joystick, track ball, mouse, and/or an electromechanical device, and/or switches, buttons, or the like for applying forces related to the movement of the probe assembly 100. In other embodiments, an HID can include force sensors such as strain gauges, which can detect forces related to a connector, for example, push, pull, and/or twist forces, for example, to steer the probe assembly 100.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following at least one of the preceding claims.

The invention claimed is:

1. An articulated probe assembly, comprising:
   a base;
   an outer support rod extending through the base;

an articulating control portion at a proximal end of the outer support rod; a steerable portion comprising a plurality of outer links coupled to a distal end of the outer support rod, the steerable portion manipulated in response to the articulating control portion;

a handle that articulates the control portion, which in turn articulates the steerable portion; and a tool support assembly comprising first and second support rods, each with a proximal end into which a tool can be inserted and further comprising a connector directly and removably coupled to proximal ends of the first and second support rods and that maintains a position of the first and second support rods from each other, the connector separate from the base by a length of the first and second support rods, and wherein the connector is constructed and arranged for removal from the support rods and replacement with a different connector having a different configuration wherein the first and second support rods are each coupled to a top surface of the base, and wherein first and second guide tubes having a different dimension than the first and second support rods are coupled to a bottom surface of the base and align with the first and second support rods, respectively, via the base.

2. The articulated probe assembly of claim 1, wherein the articulating control portion is above the base and the steerable portion is below the base.

3. The articulated probe assembly of claim 1, wherein the articulating control portion comprises a plurality of second outer links that articulate relative to each other for controlling an articulation of the outer links of the steerable portion.

4. The articulated probe assembly of claim 3, wherein the articulating control portion comprises a plurality of channels, and the outer support rod comprises a plurality of channels that are aligned with the channels of the control portion, each support rod channel and corresponding control portion channel receiving a steering cable, the steering cables constructed and arranged to control a motion of the steerable portion in response to an articulation of the second outer links relative to each other.

5. The articulated probe assembly of claim 1, wherein the articulating control portion comprises an articulating element that articulates the steerable portion relative to the control portion according to at least one degree of freedom.

6. The articulated probe assembly of claim 1, further comprising an inner rod that extends through at least a portion of the outer support rod and at least a portion of the steerable portion.

7. The articulated probe assembly of claim 6, wherein articulation of the steerable portion is controlled by a location of the inner rod.

8. The articulated probe assembly of claim 6, wherein when the inner rod is at its highest point, the steerable portion has a greatest range of motion.

9. The articulated probe assembly of claim 6, further comprising a translation assembly that translates the inner rod, wherein the inner rod translates via the translation assembly vertically within the outer support rod.

10. The articulated probe assembly of claim 1, wherein the base comprises a height adjustment gear and the outer support rod comprises a linear gear that engages with the height adjustment gear for changing a height of the outer support rod, which in turn changes a height of the steerable portion relative to the base.

11. The articulated probe assembly of claim 1, wherein the plurality of outer links of the steerable portion includes a distal link, the distal link including at least one exit port from which a tool can extend for insertion into a surrounding environment.

12. The articulated probe assembly of claim 11, wherein the surrounding environment is selected from the group consisting of: the esophagus, the gastrointestinal tract, the pericardial space, the peritoneal space, or combinations thereof.

13. The articulated probe assembly of claim 11, further including at least one side channel coupled to the distal link for receiving one or more tools.

14. The articulated probe assembly of claim 13, wherein the at least one side channel is configured to perform one or more of: slidingly receiving a shaft of a tool, guiding the shaft of a tool, providing a supporting force for a tool, or combinations thereof.

15. The articulated probe assembly of claim 1, further comprising a plurality of steering cables operably connected to the handle, wherein movement of the handle applies tension to the steering cables which in turn articulates the steerable portion.

16. The articulated probe assembly of claim 15, wherein the steering cables extend from channels in the control portion, through matching channels in the outer support rod, through channels in the steerable portion, and terminating at a distal link of the outer links.

17. The articulated probe assembly of claim 15, further comprising a cable tensioning assembly operably connecting the steering cables to the handle, wherein the cable tensioning assembly is constructed and arranged to adjust the tension in one or more of the steering cables.

18. The articulated probe assembly of claim 17, wherein the cable tensioning assembly is constructed and arranged to adjust tension in multiple cables to transition the steerable portion between an articulable state and a locked state.

19. The articulated probe assembly of claim 18, wherein the cable tensioning assembly is constructed and arranged to increase the tension applied to each and all of the steering cables to cause the steerable portion to transition from the articulable state to the locked state.

20. The articulated probe assembly of claim 18, wherein the cable tensioning assembly is biased such that the steerable portion is in the locked state.

21. The articulated probe assembly of claim 18, wherein the cable tensioning assembly comprises a button constructed and arranged to decrease the tension applied to at least one steering cable to cause the steerable portion to transition from the locked state to the articulable state.

22. The articulated probe assembly of claim 1, wherein the base is coupled to a support arm.

23. The articulated probe assembly of claim 1, further comprising an inner rod slidingly positioned within the outer support rod and a translation assembly, wherein the steerable portion comprises an articulation region, and wherein the translation assembly translates the inner rod to adjust a range of motion of the articulation region of the steerable portion by increasing or decreasing a number of the outer links capable of articulation.

24. The articulated probe assembly of claim 23, wherein the translation assembly comprises a collar that is slidingly received by the outer support rod.

25. The articulated probe assembly of claim 24, wherein the transition assembly further comprises a gear and at least one knob operably couples to the gear.

26. The articulated probe assembly of claim 24, wherein the outer support rod comprises a slot and the translation assembly comprises a connecting element that is fixedly attached to the collar and the inner rod, passing through the slot, such that the inner rod translates with the collar.

27. The articulated probe assembly of claim 24, wherein the outer support rod comprises a set of threads arranged in a helical manner about the outer support rod, wherein the collar includes a set of inner threads at a hole of the collar through which the outer support rod is positioned, and wherein the inner threads of the collar communicate with the threads of the outer support rod such that a rotation of the outer support rod causes the outer support rod to travel linearly.

28. The articulated probe assembly of claim 1, wherein the connector comprises a dogbone connector coupled between the two support rods.

29. The articulated probe assembly of claim 1, wherein at least one of the first guide tube or the second guide tube is positioned in at least one side channel of a distal link of the outer links and extending along the steerable portion, for guiding a tool extending from the proximal end of the first or second support rod to the distal link.

30. The articulated probe assembly of claim 1, wherein the first guide tube is positioned on a first side channel of the distal link and extending along the steerable portion, for guiding a first tool extending from a proximal end of the first support rod, and the second guide tube is positioned on a second side channel of the distal link and extending along the steerable portion, for guiding a second tool extending from a proximal end of the second support rod.

31. The articulated probe assembly of claim 1, wherein the outer support rod comprises a set of threads arranged in a helical manner about the outer support rod, wherein the base includes a set of inner threads at a hole of the base through which the outer support rod is positioned, and wherein the inner threads of the base communicate with the threads of the outer support rod such that a rotation of the outer support rod causes the outer support rod to travel linearly relative to the base.

\* \* \* \* \*

UNITED STATES PATENT AND TRADEMARK OFFICE
CERTIFICATE OF CORRECTION

PATENT NO. : 10,004,568 B2
APPLICATION NO. : 14/892750
DATED : June 26, 2018
INVENTOR(S) : Michael Salvatore Castro et al.

It is certified that error appears in the above-identified patent and that said Letters Patent is hereby corrected as shown below:

In the Claims

Claim 1, Column 15, Line 19, insert a -- ; -- after "configuration" and before "wherein"

Claim 25, Column 16, Line 63, delete "transition" and insert -- translation --

Claim 30, Column 18, Lines 2 - 3, delete "the distal link" and insert -- a distal link --

Claim 30, Column 18, Line 6, delete "the distal link" and insert -- a distal link --

Signed and Sealed this
Nineteenth Day of February, 2019

Andrei Iancu
*Director of the United States Patent and Trademark Office*